United States Patent [19]

Brownstein et al.

[11] 4,028,423

[45] June 7, 1977

[54] OXIDATION OF ALIPHATIC AND ALICYCLIC HYDROCARBONS

[75] Inventors: Arthur M. Brownstein, Cherry Hill, N.J.; David L. Kerr, Wilmington, Del.

[73] Assignee: Sun Oil Company, Philadelphia, Pa.

[22] Filed: Nov. 25, 1970

[21] Appl. No.: 92,834

Related U.S. Application Data

[63] Continuation-in-part of Ser. No. 722,178, April 18, 1968, abandoned.

[52] U.S. Cl. .................. 260/610 B; 260/593 P; 260/601 R; 260/632 R
[51] Int. Cl.$^2$ .............. C07C 179/02; C07C 179/06
[58] Field of Search .................. 260/610 B, 610 R

[56] References Cited

UNITED STATES PATENTS

| | | | |
|---|---|---|---|
| 2,770,637 | 11/1956 | Mitchell et al. | 260/586 |
| 2,954,405 | 9/1950 | Hock et al. | 260/610 |
| 3,300,399 | 1/1967 | Wildi et al. | 260/610 R |
| 3,316,279 | 4/1967 | Fenton | 260/597 |
| 3,634,328 | 1/1972 | Brownstein | 252/431 N |

FOREIGN PATENTS OR APPLICATIONS 1,159,006  7/1969  United Kingdom ........... 260/610 B

OTHER PUBLICATIONS

Cook, "Journal Chem. Soc.", July–Dec. 1938, pp. 1766–1767.
Moser & Thomas, Phthalocyanine Compounds, Reinhold Publishing Co., N.Y., 1963, pp. 328–336.
Kyuita, "Dokladi Akadenie Nack SSR", 148, No. 1, pp. 118–121 (Jan. 1963).

*Primary Examiner*—James O. Thomas, Jr.
*Assistant Examiner*—W. B. Lone
*Attorney, Agent, or Firm*—Donald R. Johnson; Stanford M. Back

[57] ABSTRACT

Copper polyphthalocyanine which has been activated by contact with an aromatic heterocyclic amine to form a novel complex is an effective catalyst for the oxidation of certain aliphatic and alicyclic compounds.

6 Claims, No Drawings

OXIDATION OF ALIPHATIC AND ALICYCLIC HYDROCARBONS

CROSS-REFERENCE TO RELATED APPLICATION

This application is a continuation-in-part of earlier filed application, Ser. No. 722,178, filed Apr. 18, 1968, now abandoned.

BACKGROUND OF THE INVENTION

This invention relates to a novel catalyst and to its use in an improved process for the oxidation of certain aliphatic and alicyclic hydrocarbons to form the corresponding hydroperoxides, aldehydes, ketones, acids and the like. More particularly, this invention relates to the use of a novel copper polyphthalocyanine catalyst to improve the oxidation rate of aliphatic and alicyclic compounds to form a variety of oxidation products. The terms "aliphatic" and "alicyclic" as used herein, include both saturated and unsaturated non-aromatic hydrocarbons.

U.S. Pat. No. 2,954,405 teaches the use of copper phthalocyanines as catalysts in the oxidation of substituted aromatics to form the corresponding hydroperoxides. This reference does not, however, teach or suggest the use of copper polyphthalocyanines as oxidation catalysts for aliphatic or alicyclic compounds.

SUMMARY OF THE INVENTION

It has now been found, in accordance with the present invention, that the rate of oxidation of aliphatic and alicyclic hydrocarbons to form oxidation products such as the corresponding hydroperoxides, alcohols, aldehydes, ketones and the like, can be substantially improved when there is employed as the oxidation catalyst a copper polyphthalocyanine which has been activated with an aromatic heterocyclic amine such as pyridine.

DESCRIPTION OF THE INVENTION

The catalysts employed in this process are formed by combining a copper polyphthalocyanine with an aromatic heterocyclic amine such as pyridine, quinoline, isoquinoline, triazine, pyrazine or the like. The catalyst may be prepared in one of several ways, as for example by grinding the crude, hard, brittle copper polyphthalocyanine to form a powder, washing it with a solvent such as pyridine and ethanol in order to remove copper salts, thoroughly drying the mixture in a sublimator at a temperature of about 210 to 250° C for several days in order to remove all volatile impurities, including the pyridine, and then adding a measured amount of the aromatic heterocycle amine to the pure copper polyphthaocyanine to form the novel catalyst.

Alternatively, the catalyst may be prepared by grinding and washing the copper polyphthalocyanine, using as the solvent the desired aromatic heterocyclic amine itself and then carefully drying the mixture in order to remove all but a measured amount of the amine solvent. In carrying out this latter process the drying time and temperature are dependent upon the particle size of the copper polyphthalocyanine, the coarser particles requiring more drying than do the finer particles. In general, drying the ground copper polyphthalocyanine at a temperature of 245° C for about 96 hours has provided satisfactory results.

The catalyst, when prepared by the first method described above, is preferably formed in situ by the addition of the heterocyclic amine to the oxidation reaction medium containing the previously-powdered and dried copper polyphthalocyanine. The reason for this is that when the copper polyphthalocyanine-amine catalyst is allowed to sit for more than a few months, its effectiveness has been found to be measurably diminished. This is likewise true when the catalyst is made by other methods, in which case it is necessary to reactivate the copper polyphthalocyanine with additional amine before using it.

Regardless of how the catalyst is prepared, it is important that it contain from about 7 to 200 parts by weight of aromatic heterocyclic amine for each 100 parts of copper polyphthalocyanine, and preferably from 20 to 100 parts. Within these ranges, the particular quantity of amine employed in activating the catalyst has been found to be somewhat depending upon the reaction temperature at which the oxidation is carried out: in general the amount of amine employed may be increased as the reaction temperature is decreased. Conversely, it is necessary to increase the amount of amine if higher oxidation temperatures are utilized up to an optimum temperature of about 200° C.

Should a decrease in activity of the catalyst take place with the passage of time, this activity may very readily be restored to approximately its original level by the addition of the heterocyclic amine directly to the reaction medium. Moreover, this restoration may be effected many times during the life of the catalyst without any substantial loss of catalytic activity. The amount of heterocyclic amine which must be added to restore catalytic activity will naturally vary, depending upon the amount of the copper polyphthalocyanine in the medium, the time interval, and the like. Generally, however, it is sufficient if the amine is introduced in amounts not in excess of the weight ratios employed in the formation of the original polyphthalocyanine-amine catalyst, and preferably somewhat smaller amounts of amine should be employed.

While applicants do not wish to be bound by any particular theory, it is believed that the reaction product of the copper polyphthalocyanine and the heterocyclic amine is in the form of a complex of the two components rather than a simple admixture. Evidence for this has been adduced by the fact that catalytic activity rapidly decreases with decreasing heterocyclic amine to copper polyphthalocyanine ratios, whereas in continuous operations employing initially the preferred amine to polyphthalocyanine ratio, there is no observed decline in catalytic activity at a point where successive replenishment of the mother liquor with fresh reactant would have theoretically reduced the amine content far below the accepted level.

This catalyst complex, which is distinguished by its ability to increase the rate of oxidation of aliphatic and alicyclic hydrocarbons, is a solid material at room temperature and is characterized by its high insolubility in most reaction media.

The copper polyphthalocyanine component of applicants' catalyst may be prepared in many different ways, and indeed, depending upon the manner of its preparation, may have different properties and characteristics. Thus, for example, the preparation of one form of copper polyphthalocyanine, which is formed by the reaction of pyromellitonitrile with a copper salt such as cuprous chloride, is disclosed in British Pat. No. 883,552. Briefly, this component may be prepared by various methods, as for example, by reacting an excess of pyromellitonitrile with finely divided cuprous chloride in an inert, oxygen-free atmosphere, at elevated temperatures of about 300 to 400° C and elevated pressures of about 2000 to 3000 psi for several hours. Small amounts of urea may be added, if desired, in order to neutralize any resulting hydrogen chloride. The resulting material is characterized by its dark blue color, its graphite-like consistency and its substantial insolubility in most solvents, including sulfuric acid.

Another known form of copper polyphthalocyanine is described in the Soviet journal, *Dokladi Academi Nauk*, SSR, 148, No. 1, 118–121 (January, 1963). The copper polyphthalocyanine described in that article is prepared by the reaction of pyromellitic dianhydride with urea and a copper salt such as cuprous chloride, in the presence of ammonium molybdate catalyst, and is notably soluble in concentrated sulphuric acid. This latter product is further characterized in that its I.R. spectrum shows strong carbonyl bands at 5.63 and 5.80 microns, while the copper polyphthalocyanine prepared from pyromellitonitrile shows no carbonyl bands, but does show a weak nitrile group at 4.45 microns.

The starting materials employed in the process of this invention comprise both aliphatic and alicyclic hydrocarbons. By this it is meant that the aliphatic compounds include both paraffinic and olefinic hydrocarbons, such as propylene, isobutane, isobutylene, 1-butene and hexadecane, while the alicyclic compounds include both saturated polycyclic ring compounds such as decalin and non-aromatic unsaturated ring compounds, such as cyclohexene. These compounds may be substituted by those groups which would not be oxidized by the conditions of this process, as for example nitro, nitrile, sulfone and carboxylic acid radicals.

Generally speaking, whether the starting materials are open chain or cyclic compounds, it is important to note that in the saturated compounds the secondary and/or tertiary carbon atoms are more readily oxidized by this process, while in the unsaturated hydrocarbons those carbon atoms which are to a double bond, whether they be primary, secondary or tertiary, will be readily oxidized.

The nature of the products obtained will be determined by the reaction conditions employed, and particularly the temperature. Thus, within the given temperature range discussed below, the lower the temperature, generally speaking, the greater the amount of hydroperoxide which will be formed as the principal product. As the temperature is increased, it is found that the oxidation of primary carbon atoms leads principally to the production of aldehydes and acids; the oxidation of seconary carbon atoms leads principally to the production of ketones and alcohols; while the oxidation of tertiary carbon atoms generally results either in the decomposition of the hydroperoxide to form an alcohol, or in chain scission to give a ketone and an alcohol as the principal products.

Needless to say, together with the particular temperature employed, the final product will also be a function of the nature of the starting material. Thus, for example, the oxidation of isobutane in accordance with this process at 110° C will provide the corresponding hydroperoxide, while the same oxidation carried out at 145° C will result in acetone and methyl alcohol as the principal products. From the foregoing, those skilled in the art will perceive that by the proper selection of starting material and reaction conditions within the teaching of this invention, a wide variety of oxidized organic compounds may thereby be obtained.

The process of this invention, utilizing the aforedescribed catalyst, is conveniently carried out by the rapid passage of oxygen or air through a suitable reactor, to which has first been added a mixture of the hydrocarbon substrate, the copper polyphthalocyanine-heterocyclic amine catalysts, and solvent where needed. The air or oxygen should be brought into intimate contact with the liquid phase, for example, by the use of high speed stirrers, suitable nozzles or the like.

The amount of catalyst employed will vary depending upon the nature and amount of the material to be oxidized. In general, however, the amount of catalyst may vary from about 0.05 grams to 2.0 grams of catalyst per mole of substrate, and preferably should be from 0.1 to 1.0 grams per mole of substrate.

The rate of input of oxygen or air will depend upon the temperature and pressure utilized during the oxidation. There should be provided at least an amount theoretically sufficient to convert the starting material completely to the corresponding oxidation product, and preferably an excess of this amount. It has been found that a flow rate ranging from 0.5 to 300 liters per hour is generally sufficient for most conversions. Any uncombined oxygen may, of course, be recycled to the reactor. The reaction may be effected at normal or superatmospheric pressure.

The reaction temperature may range from about 25° to 200° C but is preferably in the range of from 60° to 150° C. In those instances where the reaction temperature exceeds the boiling point of the aliphatic and alicyclic hydrocarbon substrate, it is desirable to conduct the oxidation under superatmospheric pressures. Also, if the hydrocarbon substrate is not a liquid under the conditions of the oxidation, it is desirable to employ a suitable solvent for the process. The solvent, when employed, should be liquid and inert under the oxidation conditions of the process. Suitable solvents may be selected from chlorinated and nitrated aromatic compounds, e.g. nitrobenzene, chlorobenzene and o-dichlorobenzene and the like.

The reaction is generally complete in from one to ten hours, depending upon the amount of substrate employed. However, the reaction is desirably terminated after a period of one to three hours and the products recovered.

Advantageously, small amounts of the hydroperoxide may be introduced into the reaction medium to act as a reaction initiator. Thus, for example, when cyclohexane is being oxidized, it has been found to be advantageous to add a small amount of cumyl hydroperoxide in order to initiate the reaction.

The resulting products are readiy recovered from the reaction medium by conventional methods. Thus, for example, in the oxidation of propylene, acrylic acid may be conveniently recovered by extracting the reaction mixture with aqueous alkali, acidifying the extract and diluting the free acid from the reaction mixture.

The above-described invention provides a method for the preparation of unsaturated acids, alcohols, aldehydes and the like at high rates of conversion. In addition, compounds such as ketones and hydroperoxides can be obtained under milder conditions than previously possible for similar yields.

PREPARATION OF TWO TYPES OF COPPER POLYPHTHALOCYANINE

A. Preparation of copper polyphthalocyanine from pyromellitic dianhydride (PMDA):

PMDA (184 m moles), anhydrous $CuCl_2$ (120 m moles), urea (3.60 moles) and $(NH_4)_2 MoO_4$ (0.1 g) were intimately blended and heated at 180° to 185° for 2 hours. The black solid was washed with $H_2O$ (0.5 l) and then dissolved in concentrated $H_2SO_4$ (200 ml) at room temperature. The dark solution was slowly added to cracked ice and water (3 l). A fine precipitate was readily obtained. The solids were filtered and washed with $H_2O$ until the washings were neutral. The dried solids were extracted with pyridine, and then dried with a sublimator at 240° C (0.1 m m Hg) until solids no longer appeared on the cold finger. The navy blue product was partially soluble in DMF. The I.R. spectrum closely resembles the pyromellitonitrile derived compound except for the absence of the nitrile group and the appearance of a carbonyl doublet indicative of anhydride end groups. The strong carbonyl bands suggest a low molecular weight polymer. This lower molecular weight is supported by the solubility of the compound in DMF and concentrated $H_2SO_4$.

Elemental analysis for a completely branched structure follows:
Calculated: C = 55.7 H = 0.93 N = 21.7 Cu = 11.6
Found: C = 52.1 H = 2.02 N = 20.7 Cu = 6.54
Surface area = 7.1 square meters per gram.

B. Preparation of copper polyphthalocyanine from pyromellitonitile.

A heavy-walled glass tube was charged with pyromellonitrile (11.0 m moles), $Cu_2Cl_2$ (6.5 m moles) and urea (2.0 m moles). The mixture was intimately ground in a mortar before charging. The tube was thoroughly flushed with helium and sealed. It was heated at 390° C for 19 hours. The fused, hard, black solid was extracted with pyridine and then washed alternately with ethanol and water until there was no detectable odor of pyridine or color to the washes. The purple solid was heated in a sublimator at 240° C and 0.1 to 0.5 mm HG for several days until impurities cease to sublime. The product was a navy blue, metallic powder. Yield: 2.1 g. It was insoluble in all solvents including concentraed $H_2SO_4$ at room temperature.

Elemental analysis is in accord with the proposed rectilinear structure.
Calculated: C = 55.3 H = 0.92 N = 29.0 Cu = 14.7
Found: C = 53.3 H = 1.55 N = 25.5 Cu = 14.1
Surface area of the catalyst is 6.7 square meters per gram.

EXAMPLE 1

A 50 ml resin pot is immersed in a thermostated oil bath (72° C). The pot is fitted with a hollow stirrer shaft through which oxygen can be added and dispensed through the agitated system. The apparatus is otherwise fitted with a water-cooled reflux condenser and vented to the atmosphere through a mineral oil or mercury bubbler. Oxygen pressure is maintained at about 1 atmosphere by a rapid flow-through of 60 mls/min.

Cyclohexene (200 m moles) is charged with cumene hydroperoxide (2 m moles) as a promotor and 0.25 weight percent (ca 0.1 m moles) copper polyphthalocyanine. Pyridine (57 mg) is added to the agitated system (ca 450 RPM) after all other reagents are present. A coparative run is also made wherein all of the above amounts are employed except that copper phthalocyanine and pyridine are substituted for copper polyphthalocyanine and pyridine. The yields of product are measured at 3 one hour intervals, with the following results:

Table 1

| Run | Catalyst System | Cyclohexene-3-Hydroperoxide (Mole %) | | |
|---|---|---|---|---|
| | | 1 Hour | 2 Hours | 3 Hours |
| 1 | Copper Polyphthalocyanine and Pyridine | 7.77 | 11.8 | 13.2 |
| 2 | Copper Phthalocyanine and Pyridine | 3.08 | 5.52 | 7.25 |

It will be seen by comparing the above results that the initial rate of oxidation when copper polyphthalocyanine and pyridine are employed is about twice that for copper phthalocyanine and pyridine.

EXAMPLE 2

Chlorobenzene (50 mls) is charged to a stainless steel autoclave fitted with a mechanical stirrer, along with copper polyphthalocyanine (60 mg), and pyridine (57 mg). The system is heated to 110° C, agitated and pressurized first with propylene to 300 psig, and finally with oxygen for a total final pressure of 600 psig. Oxygen is continually fed to the mixture to maintain the pressure at 600 psig. After 2 hours, acrylic acid and acrolein are obtained in good yield.

EXAMPLE 3

O-dichlorobenzene (50 mls) is charged to a stainless steel autoclave as in Example 3. The system is then charged with copper polyphthalocyanine (60 mg), and quinoline (25 mg) and cumene hydroperoxide (0.3 g). The mixture is agitated, heated to 100° C and pressurized with isobutane to 400 psig. It is then pressurized with oxygen to 700 psig. Additional oxygen is fed to the mixture over a 3 hour period to maintain the pressure at 700 psig. T-butyl hydroperoxide is formed in excellent yield as measured by $Na_2S_2O_3$-KI titration.

EXAMPLE 4

The procedure of Example 1 is repeated at 130° C using decalin in place of cyclohexene and pyrazine in place of pyridine; 1-decalone is obtained after 2 hours.

What is claimed is:
1. A process for the oxidation of hydrocarbons which comprise contacting an unsubstituted $C_3$-$C_{16}$ saturated or mono-unsaturated hydrocarbon selected from the group consisting of alkanes, alkenes, cycloalkenes and polycycloalkanes with oxygen or air at temperatures of from 25° to 200° C in the presence of a catalyst comprising a copper polyphthalocyanine and an aromatic heterocyclic amine, said amine being selected from the group consisting of pyridine, quinoline, isoquinoline, triazine, and pyrazine, wherein the weight ratio of amine to copper polyphthalocyanine is between 0.7:1 and 2:1.
2. The process according to claim 1 wherein the temperature is in the range of from 60 to 150° C.
3. The process according to claim 1 wherein the aromatic heterocyclic amine is pyridine.
4. The process according to claim 1 wherein the aromatic heterocyclic amine is quinoline.
5. The process according to claim 1 wherein the reaction is carried out in the presence of an added hydroperoxide.
6. The process according to claim 1 wherein the cycloalkene is cyclohexene and the resulting product is cyclohexene-3-hydroperoxide.

* * * * *